(12) United States Patent
Kobayashi

(10) Patent No.: US 7,419,933 B2
(45) Date of Patent: Sep. 2, 2008

(54) PRACTICAL CHIRAL ZIRCONIUM CATALYST

(75) Inventor: Shu Kobayashi, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 565 days.

(21) Appl. No.: 10/507,307

(22) PCT Filed: Mar. 11, 2003

(86) PCT No.: PCT/JP03/02860

§ 371 (c)(1),
(2), (4) Date: Nov. 3, 2004

(87) PCT Pub. No.: WO03/076072

PCT Pub. Date: Sep. 18, 2003

(65) Prior Publication Data

US 2005/0164869 A1    Jul. 28, 2005

(30) Foreign Application Priority Data

Mar. 11, 2002  (JP) .............................. 2002-066122

(51) Int. Cl.
*B01J 27/135*    (2006.01)

(52) U.S. Cl. ...................................................... 502/227
(58) Field of Classification Search .................. 502/227
See application file for complete search history.

(56) References Cited

U.S. PATENT DOCUMENTS

2001/0012906 A1    8/2001   Giera et al.

FOREIGN PATENT DOCUMENTS

| EP | 1 134 230 A1 | 9/2001 |
|----|--------------|--------|
| JP | 2001-252569 | 9/2001 |
| WO | 01/21625 | 3/2001 |
| WO | WO 01/57190 A2 | 8/2001 |

OTHER PUBLICATIONS

Suzuki et al., N., Shokubai, vol. 41, No. 6, pp. 392-394 (1999).
Ueno et al., M., CSJ: The Chemical Society of Japan Koen Yokoshu, vol. 81, No. 2, p. 1244 (2002).
Ueno et al., M., Org. Lett., vol. 4, No. 20, pp. 3395-3397 (2002).
Kobayashi et al, Journal of the American Chemical Society, 1998, vol. 120, No. 2, pp. 431-432.

*Primary Examiner*—Zinna N Davis
(74) *Attorney, Agent, or Firm*—Wenderoth, Lind & Ponack, L.L.P.

(57) ABSTRACT

A practical chiral zirconium catalyst that can maintain its high catalytic activity even after long-term storage, which is stable in air and storable for a long period of time, and recoverable and reusable after reaction, is provided.

14 Claims, No Drawings

PRACTICAL CHIRAL ZIRCONIUM CATALYST

This application is a 371 application of PCT/JP03/02860 filed Mar. 11, 2003.

TECHNICAL FIELD

The invention of the present application relates to a practical chiral zirconium catalyst that is stable in air and maintains high catalytic activity even after long-term storage. More specifically, the invention of the present application relates to a practical chiral zirconium catalyst, which is stable in air and storable for a long period of time, and which may be used effectively for asymmetric Mannich reaction, Aza Diels-Alder reaction, Strecker reaction and the like.

BACKGROUND ART

Various asymmetric synthesis reactions are known to be effective for the organic synthesis of natural substances and their analogs. Although some asymmetric catalysts used in such asymmetric synthesis reactions have high activity and promote the intended reaction with high selectivity, many are liable to decomposition and inactivation due to external causes such as oxygen, water, light and heat, and are thus unstable. Hence, most asymmetric catalysts must be prepared from stable precursors immediately before use, and asymmetric catalysts that are stable, storable for a long period of time, recoverable and reusable after reaction, are rare.

The inventors of the present application have developed and reported a chiral zirconium catalyst useful for asymmetric Mannich reaction, and the like (for example, Japanese Patent Application No. 9-197589; Ishitani, H., Ueno, M., and Kobayashi, S., J. Am. Chem., vol. 122, p. 8180 (2000)). However, such chiral zirconium catalyst was also unstable in air and in the presence of water, and use after long-term storage, as well as recovery and reuse after reaction was substantially impossible. Accordingly, in most reaction systems, the catalysts are prepared and used in situ for each reaction.

If a chiral zirconium catalyst could be prepared in advance and stored for a long period of time, the number of process steps for synthesis can be reduced, and for example, in the case of asymmetric Mannich reaction, the operation can be further simplified. Further, if the catalyst could be recovered and reused, not only will it lead to a reduction of cost for the synthesis reaction, but would also lead to a reduction in the amount of metal-containing waste solution, and is thus useful from an environmental viewpoint.

Therefore, the object of the present invention is to solve the aforementioned problems by providing a highly practical chiral zirconium catalyst, which maintains high catalytic activity even after long-term storage, is stable, and can be recovered and reused after reaction.

DISCLOSURE OF THE INVENTION

In order to solve the above-mentioned problems, the invention of the present application firstly provides a practical chiral zirconium catalyst that is stable in air and storable for a long period of time, comprising a chiral zirconium catalyst and zeolite, wherein the chiral zirconium catalyst is fixed onto the zeolite.

Further, the invention of the present application provides, secondly, the practical chiral zirconium catalyst, wherein the chiral zirconium catalyst comprises, as its component, zirconium and an optically active binaphthol compound; and thirdly, the practical chiral zirconium catalyst, wherein the chiral zirconium catalyst comprises as its component, a coordination compound.

Furthermore, the invention of the present application provides, fourthly, the practical chiral zirconium catalyst, wherein the chiral zirconium catalyst is represented by the following formula (I):

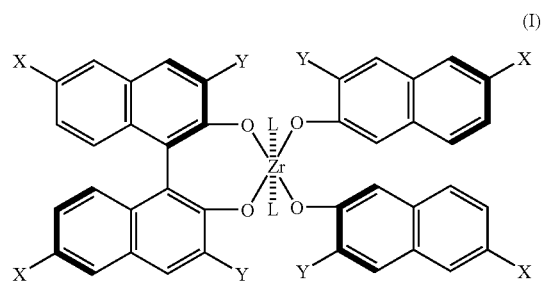

wherein, X and Y are the same as or different from each other and represent a hydrogen atom, a halogen atom or a fluorinated hydrocarbon group, at least one of them being a halogen atom or a fluorinated hydrocarbon group; and L represents a ligand; and fifthly, the practical chiral zirconium catalyst, wherein the fluorinated hydrocarbon group is a perfluoroalkyl group.

The invention of the present application sixthly provides, the practical chiral zirconium catalyst, wherein the fluorinated hydrocarbon group is a perfluoroalkyl group of 1 to 6 carbon atoms.

The invention of the present application provides, seventhly, the practical chiral zirconium catalyst, wherein the zeolite is selected from the group consisting of Molecular Sieve 3A, Molecular Sieve 4A and Molecular Sieve 5A; and eighthly, the practical chiral zirconium catalyst, wherein the chiral zirconium catalyst is fixed on zeolite by electrostatic interaction.

Furthermore, the invention of the present application ninthly provides, the practical chiral zirconium catalyst obtained by the steps of: drying Molecular Sieve by heating under reduced pressure in an inert atmosphere; mixing the Molecular Sieve with a zirconium alkoxide represented by the following formula (II):

Zr(OR)$_4$     (II)

wherein R represents a hydrocarbon group that may contain a substituent; and a (R)-BINOL represented by the following formula (III):

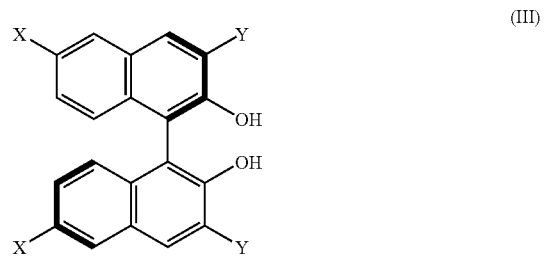

wherein X and Y may be the same as or different from each other, and represents a hydrogen atom, a halogen atom or a fluorinated hydrocarbon group, at least one of them being a halogen atom or a fluorinated hydrocarbon group.

The invention of the present application provides, as the tenth aspect, the practical chiral zirconium catalyst obtained by further mixing a coordination compound with the zirconium alkoxide and the (R)-BINOL; and as the eleventh aspect, the practical chiral zirconium catalyst, wherein the coordination compound is N-methylimidazole.

Further, the invention of the present application provides, as the twelfth aspect, a method for asymmetric Mannich reaction, comprising: reacting an imine and a silicon enolate in the presence of the above-mentioned practical chiral zirconium catalyst.

The invention of the present application provides, as a thirteenth aspect, a method for Aza Diels-Alder reaction, comprising the use of the above-mentioned practical chiral zirconium catalyst; and provides, as a fourteenth aspect, a method for Strecker reaction, comprising the use of the above-mentioned practical chiral zirconium catalyst.

BEST MODE FOR CARRYING OUT THE INVENTION

The inventors of the present application have made earnest investigations on various conditions for previously-reported chiral zirconium catalysts, and have found that by using zeolite as a retention agent, the recovery and reuse of the catalyst after reaction is made possible, and that the catalytic activity of the recycled catalyst can be maintained; thus, the present invention was accomplished.

That is, the practical chiral zirconium catalyst of the present invention is characterized in that the chiral zirconium catalyst is fixed on zeolite. The chiral zirconium catalyst used in the present invention is not particularly limited, and favorable examples include optically active binaphthol compounds represented by the following A to F:

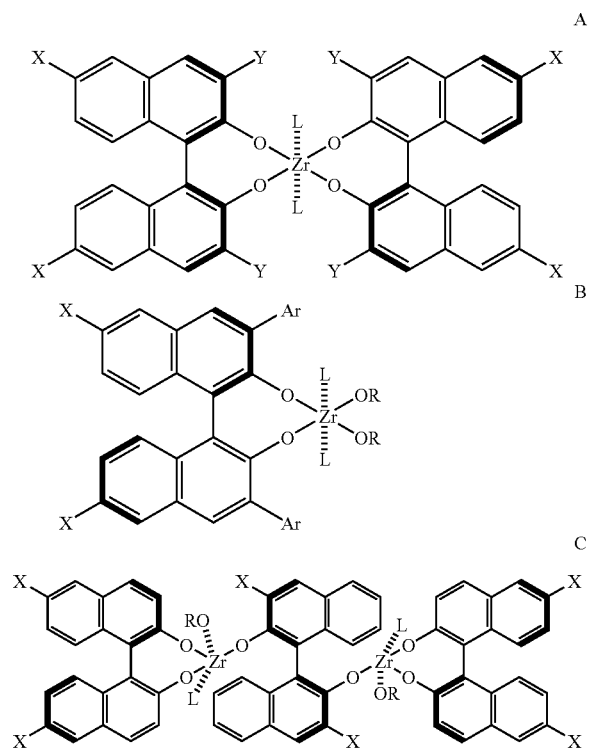

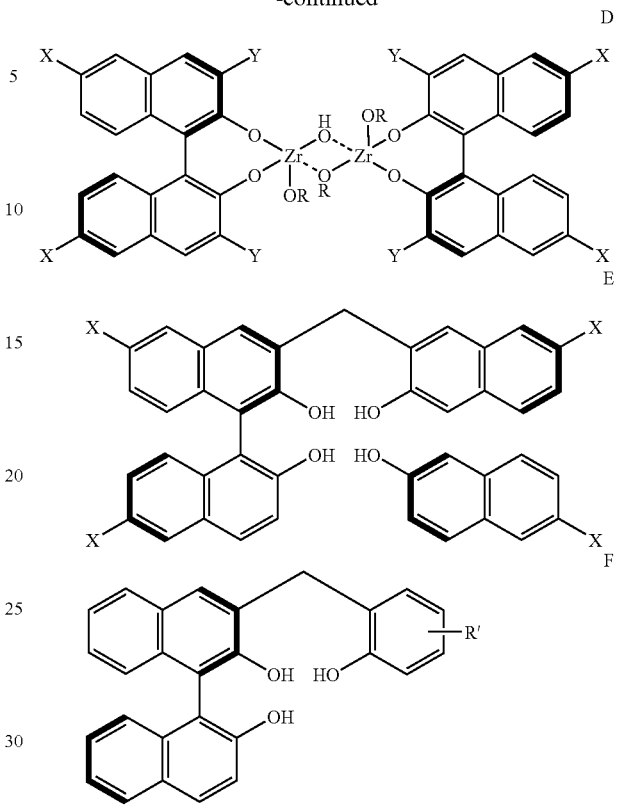

wherein X and Y are the same as or different from each other and represents a hydrogen atom, a halogen atom or a fluorinated hydrocarbon group, at least one of X and Y in the same molecule being a halogen atom or a fluorinated hydrocarbon group; R represents a hydrocarbon group that may contain a substituent; Ar represents an aromatic group that may contain a substituent; and L represents a ligand. Among such compounds, the compound represented by A is preferable, and examples of the ligand L in A include N-methylimidazole and 1,2-dimethylimidazole.

The zeolite used as a fixation carrier of the chiral zirconium catalyst used in the practical chiral zirconium catalyst of the present invention is not particularly limited. Specifically, Molecular Sieves (MS) 3A, 4A, 5A and the like, normally used as dehydrating agents, are preferable since they are inexpensive and readily available. When Molecular Sieves are used as the fixation carrier, particle diameter, pore size and the like thereof are not particularly limited, and may be appropriately selected depending on the molecular weight and the ligand of the chiral zirconium complex or the type of the solvent used. The MS are preferably used after drying by heating in vacuo so that any impurities and moisture adsorbed or absorbed are removed. Other than zeolite, similar oxides and complex oxides that show similar catalytic effect are encompassed. Specifically, divinylbenzene-crosslinked polystyrene, Drierite™ (trademark of W. A. Hammond Drierite Co.) formed with calcium sulfate and the like, Celite™ (trademark of Celite Corporation (World Minerals Inc.)), absorbents formed with $SiO_2$ and the like, are encompassed.

The practical chiral zirconium catalyst of the invention of the present application is formed by fixing the chiral zirconium catalyst to zeolite by electrostatic interaction and can be easily obtained by mixing the chiral zirconium catalyst with zeolite as a carrier, in, for example, a solution. Specifically, zeolite (such as the aforementioned MS5A) dried by heating under reduced pressure in an inert atmosphere, zirconium alkoxide represented by the following formula (II):

$$Zr(OR)_4 \qquad (II)$$

wherein R represents a hydrocarbon group that may contain a substituent (R)-BINOL represented by the following formula (III):

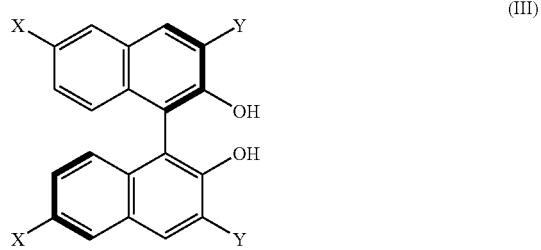

(III)

wherein X and Y are the same or different from each other and represent a hydrogen atom, a halogen atom or a fluorinated hydrocarbon group, at least one of them being a halogen atom or a fluorinated hydrocarbon group and a ligand may be added to benzene and mixed, followed by the removal of solvent and drying, to obtain the practical chiral zirconium catalyst of the present invention. The practical chiral zirconium catalyst thus obtained may be stored in the presence of air and moisture, at room temperature, and the catalytic activity is mostly maintained for a long period of time. Furthermore, when the dried catalyst is stored in an inert atmosphere such as argon, nitrogen or the like, the high catalytic activity is maintained even after several months from its preparation.

The practical chiral zirconium catalyst of the present invention can be added and used in reaction as it is; that is, in a state of being fixed to zeolite. In other words, the chiral zirconium catalyst fixed to zeolite functions as an asymmetric catalyst for various kinds of organic synthesis reactions without re-desorption. The practical chiral zirconium catalyst is present in the reaction system in such a state where it is fixed to zeolite but not dissolved in the reaction solvent, and therefore, can be recovered by general and simple operations such as filtration, removal of a solvent, and the like, after completing the reaction. The practical chiral zirconium catalyst thus recovered may be stored once more for a long period of time and used in other reactions. As apparent from the after-mentioned examples, the initial catalytic activity is mostly maintained and the reaction proceeds with high yield and stereoselectivity even when the recycled catalyst is used.

Accordingly, the use of the practical chiral zirconium catalyst of the invention of the present application not only reduces the amount of catalyst used but also reduces the amount of solvent required for the purification step for removal of the catalyst; further, since the amount of metal-containing waste solutions can be largely reduced, the practical chiral zirconium catalyst of the present invention is useful from an environmental viewpoint, as well as from an economic viewpoint. Furthermore, in asymmetric Mannich reaction using chiral zirconium catalysts previously-reported, the catalyst had to be prepared in the reaction system prior to reaction; however, this step can be omitted by using the practical chiral zirconium catalyst of the present invention, and thus the reaction is simplified.

Hereinafter, the invention of the present application will be described in more detail with reference to the Examples. It goes without saying that the invention of the present application is not limited to the following examples.

EXAMPLE

Example 1

Preparation of the Practical Chiral Zirconium Catalyst (Zeolite-fixed Chiral Zirconium Catalyst: ZiP)

Molecular Sieve 5A (powder, by Aldrich Co.) (240 mg) was suspended in benzene after sufficient drying by heating under reduced pressure in an argon atmosphere, and to this suspended, zirconium tetra-tert-butoxide (hereinafter referred to as $Zr(O^tBu)_4$, 15.3 mg, 0.04 mmol) in benzene (0.5 ml), (R)-6,6-$(C_2F_5)_2$BINOL (35.5 mg, 0.08 mmol) in benzene (1.0 ml), and N-methylimidazole (hereinafter referred to as NMI, 13.1 mg, 0.16 mmol) in benzene (0.5 ml) were added at room temperature, and stirred at 80° C. for 2 hours to prepare a benzene solution of a chiral zirconium complex. Then, the solvent was removed under reduced pressure, followed by drying at 50° C. under vacuum (0.2 mmHg) for 1 hour to obtain ZiP quantitatively (303.9 mg).

Structural analysis of the thus obtained ZiP by NMR revealed a clear spectrum similar to that obtained for a chiral zirconium catalyst prepared in situ by mixing $Zr(O^tBu)_4$, (R)-6,6-$(C_2F_5)_2$BINOL and NMI in dichloromethane.

Hereinafter, the catalyst was handled in air after drying, and was stored in a container filled with argon unless otherwise indicated.

Example 2

Mannich Reaction using Practical Chiral Zirconium Catalyst (Synthesis of (R)-Methyl 2,2'-dimethyl-(2-hydroxyphenyl) amino-3-phenyl Propionate (3a))

Enanthio-selective Mannich reaction was performed using imine (1a) synthesized from benzaldehyde and 2-aminophenol, and ketene silyl acetal (2a) derived from methyl isobutyrate.

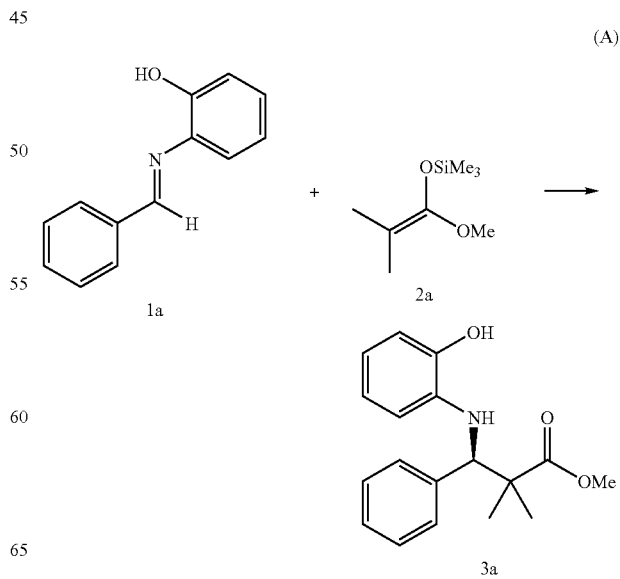

(A)

The ZiP obtained in Example 1 (152.0 mg, 0.02 mmol) was placed in a reaction vessel and NMI (0.04 mmol, 20 mol % of imine (1a)) in methylene chloride (0.5 ml) was added thereto under argon atmosphere, followed by stirring at room temperature for 30 minutes. Then, imine (1a) (0.2 mmol) synthesized from benzaldehyde and 2-aminophenol, and a methylene chloride (1.0 ml) solution of ketene silyl acetal (2a) (0.24 mmol) derived from methyl isobutyrate was added thereto, followed by stirring for 18 hours. After the reaction was quenched by adding an saturated aqueous solution of sodium hydrogen carbonate, the precipitate was filtered using Celite and extracted with methylene chloride.

After drying over anhydrous sodium sulfate, the solvent was removed under reduced pressure and the residue was treated with 8 ml of a mixed solvent of THF/1N HCl (10/1) at 0° C. for 0.5 hours. The reaction was quenched by adding a saturated aqueous solution of sodium hydrogen carbonate, followed by extraction with methylene chloride. After drying over anhydrous sodium sulfate, the solvent was removed under reduced pressure, and the residue was purified by preparative TLC on silica gel. Thus, the corresponding (R)-methyl-2,2'-dimethyl-(2-hydroxyphenyl)amino-3-phenyl-propionate was obtained (59.9 mg, quant.). Optical purity was determined by HPLC using a chiral column (CHIRALCEL, by Daicel Chemical Industries, Ltd.) (90% ee).

The yield and optical purity for compound 3a obtained in the aforementioned reaction are shown in Table 1 (entry 3).

Furthermore, the aforementioned reaction was carried out using 0 mol % (0 mmol, entry 1), 12 mol % (0.024 mmol, entry 2), and 30 mol % (0.06 mmol, entry 4) of NMI, and the results are shown in Table 1.

TABLE 1

| Entry | NMI mol % | yield % | ee % |
|---|---|---|---|
| 1 | 0 | quant | 5* |
| 2 | 12 | 94 | 87 |
| 3 | 20 | quant | 90 |
| 4 | 30 | 89 | 89 |

*Absolute configuration was S.

Identification results for compound 3a obtained in entry 3 are shown in Table 2.

TABLE 2

(R)-Methyl 2,2'-dimethyl-(2-hydroxyphenyl)amino-3-phenylpropionate (3a)

$[\alpha]_D^{24}$ + 1.4 (c 1.15, CHCl$_3$)(87% ee).
mp 112.5-114?C.
IR (KBr): 3401, 1709, 1611, 1514, 1453, 1391 cm$^{-1}$.
$^1$H NMR (CDCl$_3$): δ 1.21 (s, 3H), 1.24 (s, 3H), 3.68 (s, 3H), 4.57 (s, 1H), 6.36-6.76 (m, 4H), 7.21-7.28 (m, 5H).
$^{13}$C NMR (CDCl$_3$): δ 19.9, 24.2, 47.3, 52.3, 64.3, 113.2, 114.1, 117.6, 120.8, 127.3, 127.9, 128.3, 135.6, 138.9, 144.0, 178.0.
HPLC: Daicel Chiralpak AD, hexane/$^i$PrOH = 9/1, flow rate = 1.0 ml/min: $t_R$ = 9.3 min (3R), $t_R$ = 16.0 min (3S).
Anal. Calcd for C$_{18}$H$_{21}$NO$_3$: C, 72.22; H, 7.07; N, 4.68. found: C, 72.28; H, 7.20; N, 4.62.
HRMS: Calcd for C$_{18}$H$_{21}$NO$_3$ (M$^+$) 299.1522, found 299.1497.

Example 3

Storage Stability of Practical Chiral Zirconium Catalyst

The ZiP obtained in Example 1 was stored at room temperature in air for 0 to 13 weeks, after which it was used in the same reaction as that described in Example 2 was (Table 1, entry 3). The storage time, reaction yield and optical purity are shown in Table 3.

TABLE 3

| Storage Time week | yield % | ee % |
|---|---|---|
| 0 | quant | 90 |
| 2 | quant | 90 |
| 5 | 98 | 90 |
| 13 | 99 | 90 |

It was confirmed from Table 3 that the practical chiral zirconium catalyst of the present invention shows high stability in air and moisture and maintains catalytic activity even after being stored for 13 weeks.

When a conventional zirconium catalyst obtained from Zr(O$^t$Bu)$_4$, (R)-6,6'-(C$_2$F$_5$)$_2$BINOL and NMI was stored at room temperature in air for 1 day and used in the same reaction, significant decrease in yield and optical purity compared to those obtained immediately after preparation of the catalyst was observed. These results indicate that the high storage stability is a characteristic feature of the practical chiral zirconium catalyst of the present invention.

Example 4

Mannich Reaction using Practical Chiral Zirconium Catalyst (Synthesis of (S)-S-Ethyl-3-[(2-hydroxy-6-methylphenyl)amino]-5-methylhexane-thioate)

Enanthioselective Mannich reaction was carried out using isovaleraldehyde, 2-Amino-m-chresol, and silicon enold ether (2b) derived from an acetic acid thioester.

The ZiP obtained in Example 1 (152.0 mg, 0.02 mmol) was placed in a reaction vessel, and a N-methylimidazole (0.04 mmol) in methylene chloride (0.5 ml) of was added thereto under argon atmosphere, followed by stirring at room temperature for 30 minutes. Then, 2-Amino-m-cresol (0.2 mmol) was directly placed in the reaction vessel, and isovaleraldehyde (0.3 mmol) in methylene chloride (0.5 ml) was added thereto, followed by stirring at room temperature for 30 minutes.

A methylene chloride (0.5 ml) solution of silicon enolate (2b) (0.3 mmol) derived from acetic acid thioester used in Example 2 was added thereto at −45° C., and after stirring for 18 hours, the reaction was quenched by adding a saturated aquesou solution of sodium hydrogen carbonate (10 ml). The precipitate was filtered using Celite, and the aqueous phase was extracted with methylene chloride (10 ml three times). After drying over anhydrous sodium sulfate, the solvent was removed under reduced pressure, and the residue was purified by preparative TLC on silica gel (hexane/ethyl acetate=9/1) to obtain the corresponding (S)-S-Ethyl-3-[(2-hydroxy-6-methylphenyl)amino]-5-methylhexane-thioate (35.4 mg, 60%).

The optical purity was determined by HPLC using a chiral column (CHIRALCEL, by Daicel Chemical Industries, Ltd.) (92% ee).

The identification results for compound 3h thus obtained are shown in Table 4.

TABLE 4

(R)-S-Ethyl 3-[(2-hydroxy-6-methylphenyl)amino]-5-methylhexane-thioate (3h)

$[\alpha]D^{26}$ + 12.3 (c 0.91, CHCl$_3$)(80% ee).
IR (neat): 3356, 2957, 2871, 1681, 1588, 1472, 1366 cm$^{-1}$.
$^1$H NMR (CDCl$_3$): δ 0.81 (d, 3H, J = 6.4 Hz), 0.88 (d, 3H, J = 6.6 Hz), 1.26 (t, 3H, J = 7.4 Hz), 1.35 (dd, 2H, J = 6.6, 7.7 Hz), 1.63 (7, 1H, J = 6.7 Hz), 2.25 (s, 3H), 2.64 (dd, 1H, J = 8.0, 15.9 Hz), 2.80 (dd, 1H, J = 4.2, 15.8 Hz), 2.92 (q, 2H, J = 7.5 Hz), 3.62 (dq, 1H, J = 4.2, 7.1 Hz), 6.66 (dd, 1H, J = 0.6, 7.4 Hz), 6.76 (dd, 1H, J = 1.4, 7.8 Hz), 6.88 (t, 1H, J = 7.7 Hz).
$^{13}$C NMR (CDCl$_3$): δ 14.6, 18.1, 22.0, 23.2, 23.6, 25.1, 44.5, 48.4, 52.5, 113.3, 121.8, 124.6, 131.2, 132.5, 151.9, 200.3.
HPLC: Daicel Chiralpak OD, hexane/$^i$PrOH = 60/1, flow rate = 1.0 ml/min: $t_R$ = 14.9 min (3S), $t_R$ = 17.2 min (3R).
Anal. Calcd for C$_{16}$H$_{25}$NO$_2$S: C, 65.05; H, 8.53; N, 4.74. found: C, 65.28; H, 8.26; N, 4.93.

Example 5

Repeated Use of Practice Chiral Zirconium Catalyst (1)

For the investigation of recovery and reuse, ZiP was prepared using a larger amount of Molecular Sieve 5A (18.0 mg/mmol) than for the regular process. ZiP (392.0 mg, 0.02 mmol) was placed directly in a reaction vessel, and a methylene chloride solution (0.5 ml) of N-methylimidazole (0.04 mmol) was added thereto under argon atmosphere, followed by stirring at room temperature for 30 minutes. Then, benzaldehyde, the imine (1a) (0.2 mmol) used in Example 2, and a methylene chloride solution (1.0 ml) of ketene silyl acetal (2a) (0.24 mmol) were added thereto at −45° C., and after stirring for 18 hours, the temperature was increased to room temperature while removing methylene chloride from the reaction system using a vacuum pump.

After 3 hours, the residue was washed with hexane (5.0 ml); after leaving at rest for about 1 minute, the reaction system was released and the supernatant pentane layer was collected by a Pasteur pipette. The operation was repeated twice, and the catalyst in the precipitated layer was dried at room temperature with a vacuum pump for 3 hours and used for the next reaction.

2-Naphthol was added to the filtrate as an internal standard and the amount of (R)-6,6'-(C$_2$F$_5$)$_2$BINOL leached from ZiP was measured by HPLC. The amount of the ZiP remaining was calculated from the amount of the leached ligand, and the catalyst was used for the next reaction based on this amount. The filtrate was concentrated, and the resulting residue was accurately weighed into 5.0 ml of methanol by using a measuring flask, and the metallic zirconium leached from the ZiP was quantitatively determined by fluorescent X-ray measurement.

After the measurement, the residue was recovered and concentrated, after which it was treated with 8 ml of a mixed solvent of THF/1N HCl (10/1) at icing temperature for 0.5 hours. The reaction was quenched by adding saturated aqueous sodium hydrogen carbonate solution, followed by extraction with methylene chloride. After drying over anhydrous sodium sulfate, the solvent was removed under reduced pressure, and the residue was purified by preparative TLC on silica gel to obtain the corresponding (R)-methyl 2,2'-dimethyl-(2-hydroxyphenyl)amino-3-phenylpropionate. The optical purity was determined by HPLC using a chiral column (CHIRALCEL, by Daicel Chemical Industries, Ltd.).

In the second and subsequent reactions, the amount of ZiP was corrected for leaching and the catalyst was prepared by adding 1.5 equivalents of NMI per the corrected amount of ZiP.

The quantification of the leached (R)-6,6'-(C$_2$F$_5$)$_2$BINOL by HPLC was conducted in the following manner.

HPLC: Daicel Chiralpak AD, hexane/PrOH=9/1, flow rate=0.5 ml/min: tR=14.3 min ((R)-6,6'-(C$_2$F$_5$)$_2$BINOL), tR=20.7 min (2-naphthol). Calculated using 1.655/1 as the absorption ratio of (R)-6,6'-(C$_2$F$_5$)$_2$BINOL)/2-naphthol at a weight ratio of 1/1.

The leaching of metallic zirconium was measured by fluorescent X-ray measurement by calculating the amount of zirconium atoms leached from a calibration curve prepared using zirconium standard solutions of known concentrations.

Example 6

Asymmetric Mannich Reaction using Practical Chiral Zirconium Catalyst

Mannich reactions were conducted according to the following reaction scheme (B):

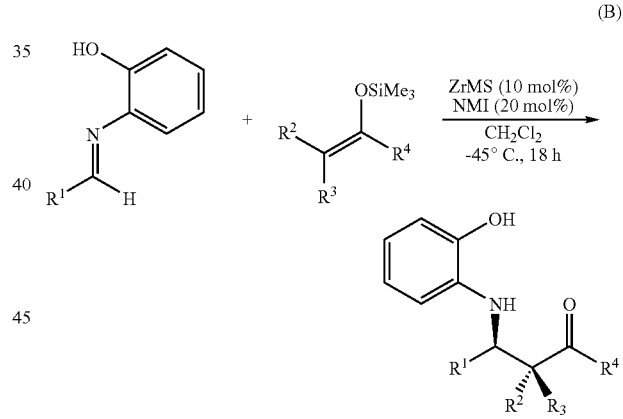

(B)

The yield, syn/anti selectivity and optical purity of the resulting products are shown in Table 5.

TABLE 5

| Entry | R$^1$ | R$^2$ | R$^3$ | R$^4$ | yield % | syn/anti | ee % |
|---|---|---|---|---|---|---|---|
| 1 | Ph | Me | Me | OMe | quant | — | 90 |
| * | | | | | quant | — | 89 |
| 2 | 1-NaPh | Me | Me | OMe | 79 | — | 90 |
| * | | | | | quant | — | 89 |
| 3 | (4-Cl)Ph | Me | Me | OMe | 96 | — | 85 |
| * | | | | | quant | — | 88 |
| 4 | Ph | H | H | SEt | 89 | — | 90 |
| * | | | | | 99 | — | 89 |
| 5 | 1-NaPh | H | H | SEt | 93 | — | 90 |
| * | | | | | quant | — | 88 |
| 6 | (4-Cl)Ph | H | H | SEt | 91 | — | 94 |
| * | | | | | 98 | — | 94 |

TABLE 5-continued

| Entry | R¹ | R² | R³ | R⁴ | yield % | syn/anti | ee % |
|---|---|---|---|---|---|---|---|
| 7 | 2-furyl | H | H | SEt | 92 | — | 89 |
| * | | | | | 96 | — | 89 |
| 8[a] | i-C₄H₉ | H | H | SEt | 60 | — | 92 |
| * | | | | | 61 | — | 92 |
| 9[b] | Ph | H | TBSO | O$^i$Pr[c] | 92 | 97/3 | 96 |
| * | | | | | 80 | 92/8 | 90 |
| 10 | Ph | BnO | H | OPh[d] | 70 | 8/92 | 89 |
| * | | | | | 74 | 5/95 | 93 |

*Chiralzirconium catalyst prepared in situ in dichbromethane under Ar was used.
[a]The imine was prepared from isovaleraldehyde and 2-amino-m-cresol (Example 4 2b).
[b]1,2-Dimethylimidazole was used instead of NMI, and toluene was used as solvent at −78° C.
[c]E/Z = >99/1 for silicone enolate.
[d]E/Z = <1/>99 for silicon enolate.

The same reactions were carried out using chiral zirconium catalysts prepared in situ by mixing Zr(O$^t$Bu)₄, (R)-6,6'-(C₂F₅)₂BINOL and NMI in dichloromethane, and the results are shown in the columns with "*"s in Table 5.

It was confirmed that Mannich reaction proceeded with high yield and high enanthioselectivity in the presence of the practical chiral zirconium catalyst of the present invention, not only for imines derived from aromatic compounds and heterocyclic aldehydes but also for imines derived from aliphatic aldehydes. In the case where α-TBSO enolate was used, the syn isomer was selectively obtained, and in the case where α-BnO enolate was used, the anti isomer was obtained with high diastereo and enanthio selectivities.

These results were corresponded to the results obtained using the conventional chiral zirconium catalyst prepared in situ.

Example 7

Repeated Use of Practice Chiral Zirconium Catalyst (2)

The imine (1a) and the ketene silyl acetal (2a) used in Example 2 were reacted in dichloromethane at −45° C. After 18 hours, the reaction vessel was warmed to room temperature, and Molecular Sieve 5A was added.

After treating under reduced pressure for 3 hours and removing the solvent and unreacted compounds, hexane was added and decantation was conducted three times. The product (3a) was isolated from the hexane solution (yield 89%, optical purity 92% ee), and the residue was treated under reduced pressure for 3 hours and then used for the second run.

Almost the same levels of yields and selectivities were obtained (second run: yield 94%, optical purity 91% ee, third run: yield 99%, optical purity 90% ee).

Example 8

Preparation of Practical Chiral Zirconium Catalyst and Asymmetric Mannich Reaction Using the Same (a) ZiP was prepared in the same manner as in Example 1, in which MS4A was used instead of MS5A, and NMI was not added.

Reaction of imine (1a) and ketene silyl acetal (2a) was carried out in the same manner as in Example 2 using the resulting ZiP, whereby a product (3a) of the asymmetric Mannich reaction was obtained with a yield of 89% and an optical purity of 82% ee.

The ZiP was stored in air at room temperature for 53 days and then used for a similar reaction, whereby the product (3a) was obtained at high yield (95%) and optical purity (80% ee).

(b) ZiP was prepared in the same manner as in Example 1, in which MS3A was used instead of MS5A, (R)-3,3'-Br₂BINOL was used instead of (R)-6,6'-(C₂F₅)₂BINOL, and NMI was not added.

Reaction of imine (1a) and ketene silyl acetal (2a) was carried out in the same manner as in Example 2 using the resulting ZiP, and a product (3a) of the asymmetric Mannich reaction was obtained with a yield of 80% and an optical purity of 97% ee.

The ZiP was stored for 12 days and then used for a similar reaction, whereby it was confirmed that both the yield (79%) and the optical purity (96% ee) were maintained.

INDUSTRIAL APPLICABILITY

As described in detail above, the invention of the present application provides a practical chiral zirconium catalyst that is stable in air and storable for a long period of time. The use of the practical chiral zirconium catalyst of the invention not only reduces the amount of catalyst used, but also the amount of purifying solvent required for removing the catalyst, as well as the amount of metal-containing waste solutions. Thus, the invention is useful not only from an economic viewpoint but also from an environmental viewpoint, as well as from the viewpoint of safety against human body. Furthermore, while in situ preparation of catalyst is required in most asymmetric Mannich reaction that use conventional chiral zirconium catalyst, by using the practical chiral zirconium catalyst of the present invention, such process step may be omitted and thus, the reaction operation may be simplified.

The invention claimed is:

1. A practical chiral zirconium catalyst that is stable in air and storable for a long period of time, which comprises a chiral zirconium catalyst comprising, as its component, zirconium and an optically active binaphthol compound, and zeolite, wherein the chiral zirconium catalyst is fixed onto the zeolite, wherein the chiral zirconium catalyst is represented by the following formula (I):

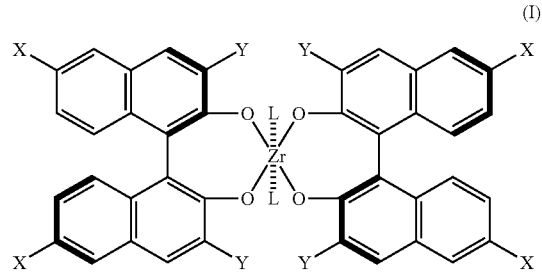

wherein, X and Y are the same as or different from each other and represent a hydrogen atom, a halogen atom or a fluorinated hydrocarbon group, at least one of them being a halogen atom or a fluorinated hydrocarbon group; and L represents N-methylimidazole or 1,2-dimethylimidazole.

2. The practical chiral zirconium catalyst of claim 1, wherein the fluorinated hydrocarbon group is a perfluoroalkyl group.

3. The practical chiral zirconium catalyst of claim 1, wherein the fluorinated hydrocarbon group is a perfluoroalkyl group of 1 to 6 carbon atoms.

4. The practical chiral zirconium catalyst of claim 1, wherein the zeolite is selected from the group consisting of Molecular Sieve 3A, Molecular Sieve 4A and Molecular Sieve 5A.

5. The practical chiral zirconium catalyst as claimed in claim 1, wherein the chiral zirconium catalyst is fixed on zeolite by electrostatic interaction.

6. A practical chiral zirconium catalyst of claim 1 obtained by the steps of:
drying Molecular Sieve by heating under reduced pressure in an inert atmosphere;
mixing the Molecular Sieve with a zirconium alkoxide represented by the following formula (II):

$$Zr(OR)_4 \quad (II)$$

wherein R represents a hydrocarbon group that may contain a substituent; and an (R)-BINOL represented by the following formula (III):

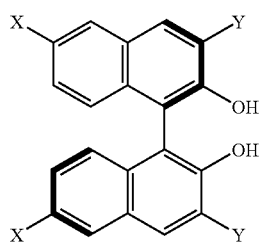

wherein X and Y may be the same as or different from each other, and represents a hydrogen atom, a halogen atom or a fluorinated hydrocarbon group, at least one of them being a halogen atom or a fluorinated hydrocarbon group.

7. The practical chiral zirconium catalyst of claim 6 obtained by further mixing a coordination compound with the zirconium alkoxide and the (R)-BINOL.

8. The practical chiral zirconium catalyst of claim 7, wherein the coordination compound is N-methylimidazole.

9. A method for an asymmetric Mannich reaction, comprising: reacting an imine and a silicon enolate in the presence of the practical chiral zirconium catalyst of claim 1.

10. A method for conducting an Aza Diels-Alder reaction which comprises employing the practical chiral zirconium catalyst of claim 1 as a catalyst for said reaction.

11. A method for conducting a Strecker reaction which comprises employing the practical chiral zirconium catalyst of claim 1 as a catalyst for said reaction.

12. A method for an asymmetric Mannich reaction, comprising: reacting an imine and a silicon enolate in the presence of the practical chiral zirconium catalyst of claim 6.

13. A method for conducting an Aza Diels-Alder reaction which comprises employing the practical chiral zirconium catalyst of claim 6 as a catalyst for said reaction.

14. A method or conducting a Strecker reaction which comprises employing the practical chiral zirconium catalyst of claim 6 as a catalyst for said reaction.

* * * * *